(12) United States Patent
Speth et al.

(10) Patent No.: US 11,027,984 B2
(45) Date of Patent: *Jun. 8, 2021

(54) UREA PROCESS WITH CONTROLLED EXCESS OF $CO_2$ AND/OR $NH_3$

(71) Applicant: Haldor Topsøe A/S, Kgs. Lyngby (DK)

(72) Inventors: Christian Henrik Speth, Lynge (DK); Per Juul Dahl, Vedbæk (DK); Annette E. Kroll Jensen, Fredensborg (DK); Niels Christian Schjødt, Hvalsø (DK); Marcus Symreng, Malmö (SE)

(73) Assignee: Haldor Topsoe A/S, Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/482,864

(22) PCT Filed: Mar. 7, 2018

(86) PCT No.: PCT/EP2018/055668
§ 371 (c)(1),
(2) Date: Aug. 1, 2019

(87) PCT Pub. No.: WO2018/162594
PCT Pub. Date: Sep. 13, 2018

(65) Prior Publication Data
US 2020/0231456 A1    Jul. 23, 2020

(30) Foreign Application Priority Data

Mar. 7, 2017    (DK) .................................. 2017 00159

(51) Int. Cl.
*C01C 1/04*    (2006.01)
*C01B 3/02*    (2006.01)
(Continued)

(52) U.S. Cl.
CPC .......... *C01C 1/0405* (2013.01); *B01D 19/001* (2013.01); *B01J 23/80* (2013.01);
(Continued)

(58) Field of Classification Search
None
See application file for complete search history.

(56) References Cited

U.S. PATENT DOCUMENTS 3,947,551 A    3/1976 Parrish
4,186,181 A    1/1980 Giammarco et al.
(Continued)

FOREIGN PATENT DOCUMENTS

| EP | 0 979 858 A2 | 2/2000 |
|----|---|---|
| WO | WO 90/06281 A1 | 6/1990 |
| WO | WO 2010/000387 A1 | 1/2010 |

OTHER PUBLICATIONS

Hiller ("Gas Production, 1. Introduction" Ullmann's Encyclopedia of Industrial Chemistry, Oct. 15, 2011, p. 403-421) (Year: 2011).*

*Primary Examiner* — Amy C Bonaparte
(74) *Attorney, Agent, or Firm* — Blank Rome LLP (57) ABSTRACT

A process for producing urea with controlled excess of $CO_2$ and/or $NH_3$. The process includes the steps of: reforming the hydrocarbon feed gas, thereby obtaining a synthesis gas comprising $CH_4$, CO, $CO_2$, $H_2$ and $H_2O$, shifting the synthesis gas, removing $CO_2$ from the synthesis gas, removing residual $H_2O$ and/or $CO_2$ from the synthesis gas, removing $CH_4$, CO, Ar and/or He, and adding stoichiometric nitrogen to produce $NH_3$ to the synthesis gas, synthesizing $NH_3$ to obtain a $NH_3$ product, and adding at least part of the product $CO_2$ and at least part of the $NH_3$ product to a urea synthesis step to make a urea product. The amount of excess $CO_2$ and/or $NH_3$ is controlled by adjusting the steam/carbon in the reforming step and/or the $H_2O$ addition upstream the (Continued)

shift step and/or adjusting the inlet temperature to at least one or more shift steps.

14 Claims, 2 Drawing Sheets

(51) Int. Cl.
 *B01D 19/00* (2006.01)
 *B01J 23/80* (2006.01)
 *C01B 3/48* (2006.01)
 *C01B 3/52* (2006.01)
 *C07C 273/10* (2006.01)

(52) U.S. Cl.
 CPC ............... *C01B 3/025* (2013.01); *C01B 3/48* (2013.01); *C01B 3/52* (2013.01); *C01C 1/0488* (2013.01); *C07C 273/10* (2013.01); *C01B 2203/0244* (2013.01); *C01B 2203/0283* (2013.01); *C01B 2203/048* (2013.01); *C01B 2203/0415* (2013.01); *C01B 2203/068* (2013.01); *C01B 2203/1076* (2013.01); *C01B 2203/1241* (2013.01); *C01B 2203/1258* (2013.01); *C01B 2203/169* (2013.01)

(56) References Cited

U.S. PATENT DOCUMENTS

| 4,193,776 | A | 3/1980 | Wasala et al. |
| 6,015,450 | A | 1/2000 | Joshi et al. |
| 2004/0028595 | A1 | 2/2004 | Davey et al. |
| 2007/0299144 | A1* | 12/2007 | Davey ................. C07C 29/1518 518/703 |
| 2011/0101279 | A1* | 5/2011 | Schiodt .................... C01B 3/16 252/373 |
| 2014/0170052 | A1 | 6/2014 | Iaquaniello et al. |
| 2016/0115017 | A1 | 4/2016 | Ostuni et al. |
| 2019/0039886 | A1* | 2/2019 | Kroll Jensen .......... B01J 23/005 |
| 2019/0382277 | A1* | 12/2019 | Speth ..................... C01B 3/025 |

* cited by examiner

Fig 1

Fig. 2

UREA PROCESS WITH CONTROLLED EXCESS OF $CO_2$ AND/OR $NH_3$

Following today's demand and competitiveness in ammonia production and related UREA production, significant efforts have been put into developing optimized production, with the objective to improve overall energy efficiency, reduce environmental impact and reduce capital cost.

In a first aspect of the present invention is provided a UREA process which enables an improved control of $CO_2$ output In a second aspect of the present invention is provided a process resulting in a highly cost efficient, environmental friendly and highly reliable UREA production.

These and further advantages are achieved by a process for producing UREA, said process comprising the steps of:

Optionally purification of a hydrocarbon feed gas removing Sulphur and/or chloride components if present, reforming the hydrocarbon feed gas in a reforming step where the steam/carbon ratio is less than 2.6 thereby obtaining a synthesis gas comprising $CH_4$, CO, $CO_2$, $H_2$ and $H_2O$, optionally adding $H_2O$ to the synthesis gas from the reforming step maintaining an overall steam/carbon less than 2.6, shifting the synthesis gas in a shift section comprising one or more shift steps preferably in series, optionally washing the synthesis gas leaving the section with water, removing $CO_2$ from the synthesis gas in a $CO_2$ removal step to obtain a synthesis gas with less than 500 ppm $CO_2$, preferably less than 20 ppm $CO_2$ and a $CO_2$ product gas, removing residual $H_2O$ and/or $CO_2$ from the synthesis gas preferably in an absorbent step, removing $CH_4$, CO, Ar and/or He preferably in a nitrogen wash unit and adding stoichiometric nitrogen to produce $NH_3$ to the synthesis gas, synthesizing $NH_3$ to obtain a $NH_3$ product, adding at least part of the product CO2 and at least part of the NH3 product to a UREA synthesis step to make a UREA product, Wherein the amount of excess $CO_2$ and/or $NH_3$ is controlled by adjusting the steam/carbon in the reforming step and/or adjusting the $H_2O$ addition upstream and/or in between the shift steps and/or adjusting the inlet temperature to at least one of the one or more shift steps.

A steam/carbon ratio of less than 2.6 has several advantages in relation to the present invention. For example, reducing steam/carbon ratio on a general basis leads to reduced feed plus steam flow through the reforming section and the downstream cooling and synthesis gas preparation sections.

Low steam/carbon ratio in the reforming section and shift section enables higher syngas throughput compared to high steam/carbon ratio. Nitrogen added via a Nitrogen wash enables higher syngas throughput compared to adding nitrogen in the reforming section. No methanation section removes the hydrogen consumption related to this section resulting in loss of ammonia product, reduces the resulting inert methane content in the synthesis gas to be removed in the nitrogen wash and using an inert free gas in the ammonia synthesis section enables higher throughput in the ammonia synthesis section Reduced mass flow through these sections means smaller equipment and piping sizes. The reduced mass flow also results in reduced production of low temperature calories, which can often not be utilised. This means that there by the present invention is a potential for both lower CAPEX and OPEX.

The applicant's invention within UREA production technology which may be applied together with the new generation state-of-the-art catalysts ensures highly cost efficient, environmental friendly and highly reliable ammonia and UREA production.

Known ammonia/UREA plants rely on maximum steam reforming with a high steam/carbon >2.6. In such known setups it is not possible to control and adjust the $CO_2/NH_3$ ratio which thus is defined by the feed gas composition which usually leads to an excess $CO_2$ which is vented or to the need to use some of the synthesis gas as fuel instead of in the ammonia production.

By adjusting the overall steam/carbon from a level which is lower than steam/carbon 2.6 it is possible to obtain a stoichiometric ratio between $CO_2$ and $NH_3$ for the UREA production and thus avoid excess $CO_2$ or excess $NH_3$. The need to produce more synthesis gas needed for the ammonia production or venting $CO_2$ can thus be avoided by the present method.

Excess $CO_2$ and excess $NH_3$ is $CO_2$ and $NH_3$ not used in the UREA synthesis.

A steam/carbon ratio of less than 2.6 may however also have disadvantages. The present invention addresses some of these. It is well known that a shift reaction cannot be performed without formation of by-products, the main by-products being methanol and to a lesser extent methyl formate and higher alcohols. In an ammonia process of known art these by-products will be partly condensed out when water is condensed out from the synthesis gas prior to a $CO_2$ removal step. The part of the methanol which is not condensed out will be absorbed together with the $CO_2$ in the $CO_2$ absorber and ends up in the $CO_2$ product. The typical methanol content in the $CO_2$ product is 500 to 1000 ppm. The by-products including methanol entering the $CO_2$ removal step of known processes thus contaminates the $CO_2$ product which may give problems if the $CO_2$ is used in a downstream process unit, such as a UREA process, or if the $CO_2$ is released to atmosphere as the by-products counts as VOCs. A further problem of the know techniques is that methyl formate is detrimental to important components in $CO_2$ absorption liquids used in many $CO_2$ removal step, resulting in less capacity and high replacement cost.

Furthermore, formation of by-products represents a loss of overall process efficiency. For a fixed feed gas flow, less product will be made with increasing by-product formation. It may be important to reduce the by-product formation for this reason alone.

The amount of by-products formed in a shift reaction step increases with decreasing steam/carbon ratio. By adding all or part of the steam stream from the process condensate stripper to the synthesis gas downstream the reforming step, e.g. prior to the last shift step of the one or more shift steps the present invention utilises that some byproducts are formed as a result of equilibrium reactions, for example the main by-product methanol, and that other by-products are partly converted into hydrocarbons, CO, $CO_2$, $H_2$ and $H_2O$ when passing a shift reaction step. Thus, the present invention provides a process where the by-products formed in the shift section can be recycled to the inlet, or between two shift steps of the shift section. For equilibrium reactions this concept will almost completely stop further formation of that particular by product. The remaining non equilibrium by product reactions will be partly converted into hydrocarbons, CO, $CO_2$, $H_2$ and $H_2O$, components which will either end up as product, recycle synthesis gas, off-gas which can be utilised as heat source for the process and water.

The present process may further comprise that,

The one and more shift steps comprise one or more high temperature (HT) shift steps, using a promoted zinc-aluminum oxide based catalyst, with possibility for cooling and/or steam addition in between.

In many of today's ammonia processes steam is added at various steps in especially the reforming and shift step. This may confuse what is meant by steam to carbon ratio at a given position in a process. In the industry and according to the present application steam/carbon ratio is typically understood as the total amount of mol water added prior to or directly to a process step divided by the mol hydrocarbon in the feed stream. It is further understood that internal recycle streams in this context also counts as feeds streams. As an example, part of the water (steam or liquid) can be added prior to a pre-reforming step, prior to the reforming step and prior to a shift step. Steam/carbon (by the definition) is for example thus increased in each steps, for example from 0.52 to 0.6 and further on to 1.0. However, it is important to note that the synthesis gas composition after the first process step cannot be used to determine the steam/carbon ratio (by the definition) as part of the hydrocarbon may have been converted and/or oxygen may have been added. When the term steam/carbon is used in this application the meaning is the typically industry definition described above.

High temperature shift is defined as a process step where a synthesis gas containing CO, $CO_2$, $H_2$ and $H_2O$ undergoes the shift reaction in the temperature range from 300° C. to 600° C. One and more shift steps may comprise one or more high temperature (HT) shift steps, using a promoted zinc-aluminum oxide based catalyst, with possibility for cooling and/or steam addition in between.

Medium temperature (MT) shift is defined as a process step where a synthesis gas containing CO, $CO_2$, $H_2$ and $H_2O$ undergoes the shift reaction in the temperature range from 190-360° C. One and more shift steps may comprise one or more medium temperature (MT) shift steps, using a Copper-zinc-aluminum oxide based catalyst or a promoted copper-zinc-aluminum oxide based catalyst, with possibility for cooling and/or steam addition in between.

Low temperature shift is defined as a process step where a synthesis gas containing CO, $CO_2$, $H_2$ and $H_2O$ undergoes the shift reaction in the temperature range from $T_{dew}$+15-290° C., such as, 180-280° C. For example, the low temperature shift inlet temperature is from Td w+15-250° C., such as 190-210° C. One and more shift steps may comprise one or more low temperature (LT) shift steps, using a Copper-zinc-aluminum oxide based catalyst or a promoted copper-zinc-aluminum oxide based catalyst, with possibility for cooling and/or steam addition in between Depending on the intended amount of excess $CO_2$ and/or $NH_3$ the one or more shift steps may be selected to be HT, MT, LT according to the invention.

A reforming section may comprise one or more reforming steps such as a pre-reformer and an ATR step.

A shift section may comprise one or more shift steps.

In a conventional ammonia plant the standard use of iron based HT shift catalyst requires a steam/carbon ratio of around 3.0 to avoid iron carbide formation.

$$5Fe_3O_4 + 32CO \leftrightarrow 3Fe_5C_2 + 26CO_2 \quad (1)$$

Formation of iron carbide will weaken the catalyst pellets and may result in catalyst disintegration and pressure drop increase.

Iron carbide will catalyse Fischer-Tropsch by-product formation $$nCO + (n+m/2)H_2 \leftrightarrow C_nH_m + nH_2O \quad (2)$$

The Fischer-Tropsch reactions consume hydrogen, whereby the efficiency of the shift section is reduced.

However, according to some embodiments of the present invention a non Fe-catalyst may be used, such as a promoted zinc-aluminum oxide based catalyst. For example, the Topsee SK-501 Flex™ HT shift catalyst which enables operation of the reforming section and HT shift section at a steam/carbon ratio down to 0.3.

Thus the present process operating at a steam/carbon ratio down to 0.3 is in contrast to today's traditional ammonia plants which are based on reforming and/or HT shift sections operating at a steam/carbon ratio of 2.6 or higher. In advantageous embodiments of the process the zinc-aluminum oxide based catalyst comprises a mixture of zinc aluminum spinel and zinc oxide in combination with an alkali metal selected from the group consisting of Na, K, Rb, Cs and mixtures thereof, and optionally in combination with Cu. The catalyst may have a Zn/Al molar ratio in the range 0.5 to 1.0 a content of alkali metal in the range 0.4 to 8.0 wt % and a copper content in the range 0-10% based on the weight of oxidized catalyst.

The HT shift catalyst used according to the present process is not limited by strict requirements to steam to carbon ratios, which makes it possible to reduce steam/carbon ratio in the shift section as well as the reforming section.

The present process may further comprise one or more of the following steps:
  the one or more shift step in series is any combination of HT shift, medium temperature (MT) shift and low temperature (LT).
  Optionally remove methanol from the shift outlet gas in a water wash
  Remove $CO_2$ from the shift outlet gas/water wash outlet gas down to a level lower than 500 ppm preferably down to below 20 ppm.
  Remove residual $CO_2$ and $H_2O$ from the gas leaving the $CO_2$ removal section in a molecular sieve dryer section.
  Remove $CH_4$, CO and inerts such as Ar and He from the gas leaving the molecular sieve dryer section in a nitrogen wash section and adjust the $N_2/H_2$ ratio to approximate 3 as needed for the ammonia synthesis.
  Convert the adjusted outlet gas from the nitrogen wash to ammonia in an inert free ammonia synthesis section.

In preferred embodiments the reforming step comprises at least an autothermal reformer (ATR).

As the requirements to the steam/carbon ratio in the shift steps e.g. HT shift step by the present process is significantly reduced compared to known technologies it is possible by the present invention to reduce steam/carbon ratio through the front end to e.g. 0.6 or as low as possible dependent on the possible shift solutions. An advantage of a low steam/carbon ratio to the ATR and in the overall process is that smaller equipment is required in the front-end due to the lower total mass flow through the plant.

The carbon feed for the ATR is mixed with oxygen and additional steam in the ATR, and a combination of at least two types of reactions take place. These two reactions are combustion and steam reforming.

Combustion Zone:

$$2H_2 + O_2 \leftrightarrow 2H_2O + \text{heat} \quad (3)$$

$$CH_4 + 3/2O_2 \leftrightarrow CO + 2H_2O + \text{heat} \quad (4)$$

Thermal and Catalytic Zone:

$$CH_4 + H_2O + heat \leftrightarrow CO + 3H_2 \quad (5)$$

$$CO + H_2O \leftrightarrow CO_2 + H_2 + heat \quad (6)$$

The combustion of methane to carbon monoxide and water (4) is a highly exothermic process. Excess methane may be present at the combustion zone exit after all oxygen has been converted.

The thermal zone is part of the combustion chamber where further conversion of the hydrocarbons proceeds by homogenous gas phase reactions, mostly (5) and (6). The endothermic steam reforming of methane (5) consumes a large part of the heat developed in the combustion zone.

Following the combustion chamber there may be a fixed catalyst bed, the catalytic zone, in which the final hydrocarbon conversion takes place through heterogeneous catalytic reactions. At the exit of the catalytic zone, the synthesis gas preferably is close to equilibrium with respect to reaction (5) and (6).

The steam/carbon ratio in the reforming section may be 2.6-0.1, 2.4-0.1, 2-0.2, 1.5-0.3, 1.4-0.4, such as 1.2, 1.0 or 0.6.

In advantageous embodiments the space velocity in the ATR is low, such as less than 20.000 $Nm^3$ $C/m^3/h$, preferably less than 12.000 $Nm^3$ $C/m^3/h$ and most preferably less 7000 $Nm^3$ $C/m^3/h$. The space velocity can be defined as the volumetric carbon flow per catalyst volume and is thus independent of the conversion in the catalyst zone.

In preferred embodiments the temperature in the HT shift step is in the range 300-600° C., such as 320-470° C. This means that according to the present process it is possible to run a high temperature shift reaction on a feed with much lower steam/carbon ratio than possible by known processes. For example, the high temperature shift inlet temperature may be 300-400° C., such as 320-380° C.

Preferably a preformer is provided as part of the reforming section upstream for example an ATR. In the preformer all higher hydrocarbons can be converted to carbon oxides and methane, but also for light hydrocarbons the preformer is advantageous. Providing the preformer may have several advantages including reducing the required $O_2$ consumption in the ATR and allowing higher inlet temperatures to the ATR since cracking risk by preheating is minimized. Thereby the ignition conditions are reached. Furthermore, the preformer may provide an efficient sulphur guard resulting in a practical sulphur free feed gas entering the ATR and the downstream system. The preforming step may be carried out at temperatures between 300-650° C., preferably 390-480° C.

In various embodiments a fired heater is used for preheating the natural gas feed, the preformer and ATR feed and for steam superheating. The necessary heat may be generated by burning a mixture of natural gas, waste gas (from the $N_2$ wash), off gas (from the inert vent gas separator) and flash gas (from the $CO_2$ removal section).

The low steam/carbon ratio may result in a lower than optimal shift conversion which means that it in some embodiments may be advantageous to provide one or more additional shift steps. The one or more additional shift steps may include a further HT shift, a MT shift and/or a LT shift. Generally speaking, the more converted CO in the shift steps the more gained $H_2$ and the smaller front end required.

This is also seen from the exothermic shift reaction given below $$CO + H_2O \leftrightarrow CO_2 + H_2 + heat \quad (7)$$

Steam may optionally be added to any of the shift steps such as before the one or more HT shifts, MT shift or LT shift steps in order to maximize performance of said following MT and/or LT shift steps.

Preferably the MT and LT shift steps may be carried out over promoted copper/zinc/aluminia catalysts. For example, the low temperature shift catalyst type may be LK-821-2, which is characterized by high activity, high strength, and high tolerance towards sulphur poisoning. A top layer of a special catalyst may be installed to catch possible chlorine in the gas and to prevent liquid droplets from reaching the shift catalyst.

The MT shift step may be carried out at temperatures at 190-360° C.

The LT shift step may be carried out at temperatures at $T_{dew}+15$-290° C., such as, 200-280° C. For example, the low temperature shift inlet temperature is from $T_{dew}+15$ 250° C., such as 190-210° C.

Reducing the steam/carbon ratio leads to reduced dew point of the process gas, which means that the inlet temperature to the MT and/or LT shift steps can be lowered. A lower inlet temperature can mean lower CO slippage outlet the shift reactors.

It is well known that HT/MT/LT shift catalysts are prone to produce methanol as byproduct. Such byproduct formation can be reduced by increasing steam/carbon. The $CO_2$ wash following the HT/MT/LT shifts requires heat for regeneration of the $CO_2$ absorption solution. This heat is normally provided as sensible heat from the process gas but this is not always enough. Typically, an additional steam fired reboiler is providing any missing heat. Optionally adding steam to the process gas can replace or reduce the size of this additional steam fired reboiler and simultaneously ensures reduction of byproduct formation in the HT/MT/LT shifts section.

The methanol formation in the HT/MT/LT shift steps is an equilibrium reaction. This means that methanol inlet a shift step will reduce the formation of methanol in said step and it further means that the last shift step typically will determine the methanol content in the synthesis gas leaving the shift section.

Part of the methanol formed by the HT/MT/LT shift catalyst is dissolved in the process condensate when the process gas is cooled prior to the $CO_2$ removal step. Further methanol can optionally be removed from the synthesis gas in a water wash to be placed downstream the cooling section just upstream the $CO_2$ removal step. If the methanol content in the $CO_2$ product is still too high this can be washed out with water.

The process condensate and the optionally washing water may be send to a process condensate stripper, where the dissolved shift byproducts and other dissolved gases are stripped off using steam. Up to more than 99% of the shift product will be removed from the process condensate and leave the process condensate stripper together with the steam. If at least part of this so called stripper steam (steam stream), now containing the main part of the shift byproduct is added to synthesis gas in the shift section prior to the last shift step it will have the effect that the net byproduct formation for especially equilibrium reactions is reduced by up to 99%, typically by 80%. To avoid build-up of higher alcohols in the circulation of shift byproducts around the shift section it may be required to purged part of the stripper steam. This purging part can be used as process steam for the reforming section. The carbon components in the stream is thus recycled and used as feed.

In preferred embodiments the stripper steam is added to the synthesis gas downstream the reforming section at the inlet of a shift section containing two high temperature shift steps (or e.g. HTS+MTS steps depending on the desired amount of excess $CO_2$ and/or $NH_3$) in series with cooling in between.

In many advantageous embodiments a $CO_2$ removal step may be carried out after/downstream the one or more shift steps. In standard design the $CO_2$ content is 500 vppm in the treated gas.

In preferred embodiments a $CO_2$ removal step may be used to bring the $CO_2$ content down to less than 400 vppm $CO_2$, such as below 100 vppm or in some preferred embodiments down to 20 vppm or below.

The process may further comprise a washing step, preferably a $N_2$ wash. The $N_2$ wash may serve several purposes such as purification of the syngas as well as to add the stoichiometric required nitrogen for a downstream ammonia synthesis.

The nitrogen for the $N_2$ wash unit (NWU) may be supplied by an air separation unit (ASU) which separates atmospheric air into its primary components nitrogen and oxygen. The oxygen is used in the ATR and the nitrogen in the NWU.

After the shift section and $CO_2$ removal unit the gas may contain residual CO and $CO_2$ together with small amounts of $CH_4$, Ar, He and $H_2O$.

$CO_2$ and $H_2O$ are preferably removed before the $N_2$ wash because they otherwise would freeze at the low operating temperature of the $N_2$ wash. This may for example be done by adsorption in a molecular sieve dryer consisting of at least two vessels one in operation while the other is being regenerated. Nitrogen may be used as dry gas for regeneration.

In the NWU the syngas is washed by liquid nitrogen in a column where $CH_4$, Ar, He and CO are removed. The purified syngas preferably contains only ppm levels of Ar and $CH_4$.

The waste gas containing the impurities together with some lost nitrogen may advantageously be used as fuel in the fired heater.

After the NWU, nitrogen gas may be added to the process stream in order to adjust the $N_2$ content to a preferred $H_2/N_2$ ratio of 3 in the make-up stream to the ammonia synthesis loop.

Because the purified syngas now only contains $H_2$ and $N_2$ in the correct stoichiometric ratio for ammonia synthesis plus ppm levels of Ar and $CH_4$ the ammonia synthesis section can be considered inert free.

An ammonia synthesis loop is defined as inert free when it is not required to purge gas from the loop because the build-up of inerts is negligible without such purge.

Thus, the present invention allows a detail control of a UREA process and plant wherein the amount of excess $CO_2$ and/or NH3 is adjusted by adjusting the steam/Carbon in the reforming steps and/or the water addition in relation to the one or more shift steps and/or by adjusting the inlet temperature of the shift steps. In selecting the inlet temperature of the shift steps it is possible to choose between HTS, MTS and LTS to adjust the CO2 production. However, it is also possible to vary the inlet temperature within the temperature ranges for given shifts steps. I.e. if a process and plant is chosen having a HTS step followed by at MTS step the amount of excess $CO_2$ and/or $NH_3$ can be adjusted by varying the inlet temperature at one or both of the shift steps while further adjusting steam addition to one or both of the shift steps if needed in order to achieve the desired $CO_2$, UREA and $NH_3$ output needed.

Furthermore, the present application relates to a plant arranged to carry out the process described herein. A plant may comprise the means for: feed purification, reforming, shift, CO2 removal, wash of the synthesis gas, NH3 synthesis, UREA synthesis as well as the means to control the steam/carbon and/or steam addition and/or temperature control of one or more shift steps.

The invention is further explained by examples 1 and 2 together with the accompanying figures. Examples and figures are provided to exemplify the invention and are not to be construed as limiting to the invention.

Figure 1:
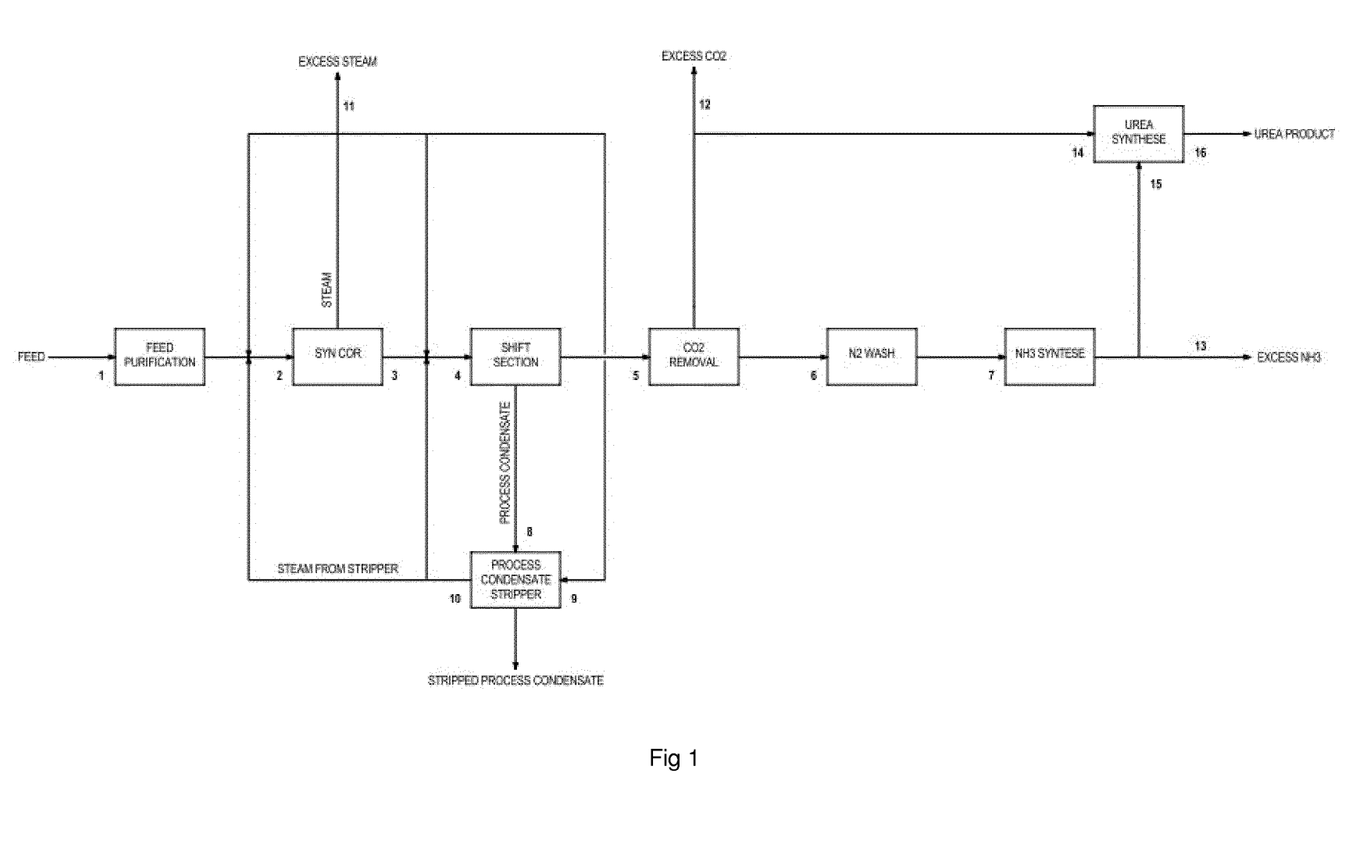

FIG. 1 shows a schematic flow diagram of an embodiment of the present invention. The numbers given in the figure corresponds to the positions given in the tables relating to the two examples.

Figure 2:
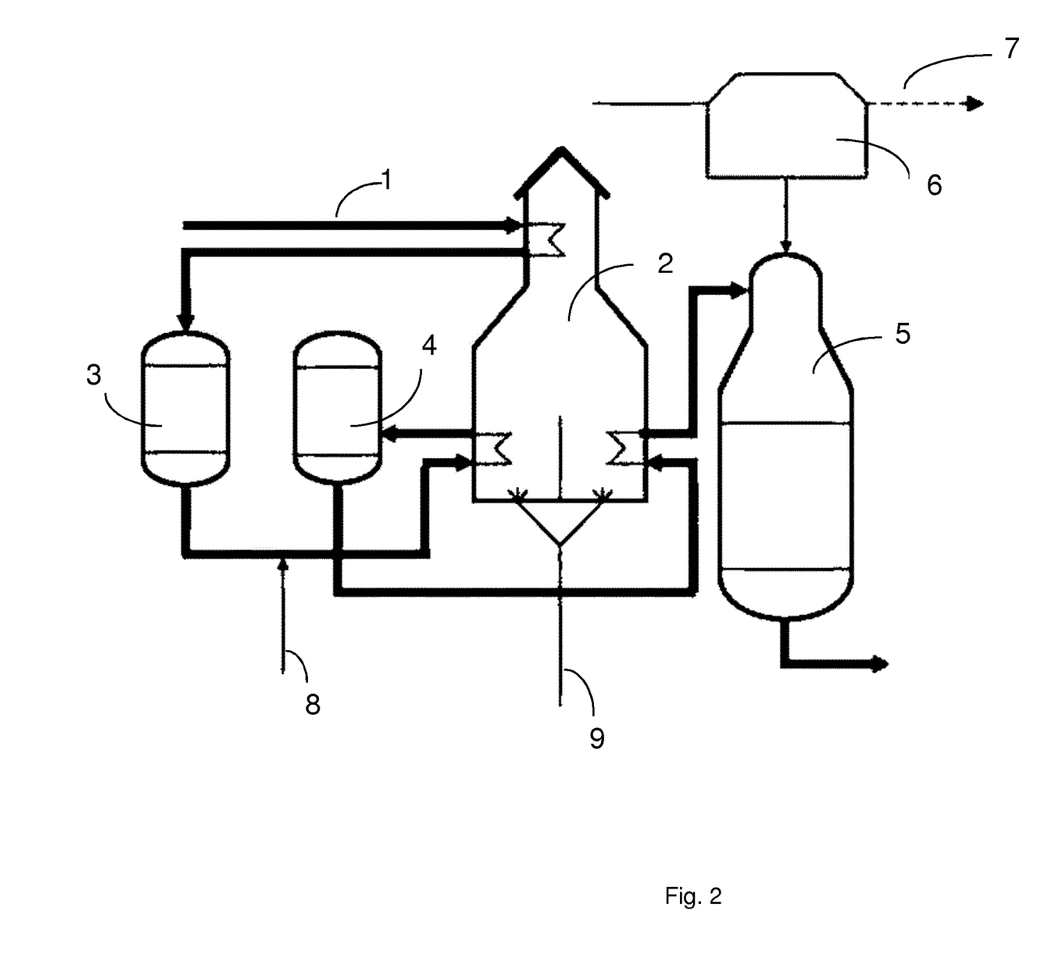

FIG. 2 shows details of an embodiment of the feed purification and SynCOR steps of FIG. 1. Feed 1, e.g. natural gas and hydrogen, is heated in a fired heater 2, where after it is treated 3 by hydrogenation and/or sulfur removal. The hydrogenated/sulfur reduced stream may be heated again and further processed by pre-reforming in a pre-reformer 4. The stream obtained by the pre-reforming is then reformed in a SynCOR step comprising an auto thermal reforming (AIR) step 5. The SynCOR step may be provided with oxygen from an air separation unit (ASU) 6. Nitrogen may be led from the ASU by 7. Steam may be added via 8 and fuel may be supplied for heater by 9.

EXAMPLE 1 FULL UREA PRODUCTION

The below positions refer to the inlet of the units.

TABLE 1

Flows and operating conditions for FIG. 1

| | Position | | | | | | | | |
|---|---|---|---|---|---|---|---|---|---|
| | Pos. 1 | Pos. 2 | Pos. 3 | Pos. 4 | Pos. 5 | Pos. 6 | Pos. 7 | Pos. 8 | Pos. 9 |
| Temp., ° C. | 380 | 465 | 360 | 330 | 73 | 20 | 46 | 45 | 381 |
| Pressure, kg/cm² g | 47.9 | 42.4 | 37.1 | 37.1 | 34.3 | 33.6 | 185 | 51.5 | 45.9 |
| Flow, Nm³/h | 137,123 | 211,944 | 465,894 | 608,589 | 471,813 | 356,204 | 440,547 | 139,546 | 89,309 |

| | Position | | | | | | |
|---|---|---|---|---|---|---|---|
| | Pos. 10 | Pos. 11 | Pos. 12 | Pos. 13 | Pos. 14 | Pos. 15 | Pos. 16 |
| Temp., ° C. | 256 | 380/172 | 50 | −32 | 50 | 20 | |
| Pressure, kg/cm² g | 43.8 | 45.9/4.6 | 0.5 | 8.2 | 0.5 | 32.2 | |
| Flow, Nm³/h | 97,924 | 9,731/26,591 | 0 | 0 | 119,576 | 219,658 | 109,675 |

TABLE 2

Stream compositions, Positions refer to FIG. 1

| Comp., Mole % | Pos. 1 | Pos. 2 | Pos. 3 | Pos. 4 | Pos. 5 | Pos. 6 | Pos. 7 | Pos. 8 | Pos. 9 |
|---|---|---|---|---|---|---|---|---|---|
| Ar | | | 0.07 | 0.05 | 0.07 | 0.09 | | | |
| C$_2$H$_6$ | 0.06 | 0.04 | | | | | | | |
| CH$_4$ | 90.83 | 58.76 | 1.25 | 0.96 | 1.24 | 1.63 | | | |
| CO | | | 21.41 | 16.39 | 1.35 | 1.75 | | | |
| CO$_2$ | | | 4.10 | 3.18 | 23.78 | 20 ppm | | 0.30 | |
| H$_2$ | 3.25 | 2.11 | 52.43 | 40.15 | 71.52 | 94.20 | 75.00 | 0.03 | |
| N$_2$ | 5.86 | 3.79 | 1.73 | 1.32 | 1.70 | 2.26 | 25.00 | | |
| CH$_3$OH | | | | 0.12 | 0.02 | | | 0.53 | |
| NH$_3$ | | | | | | | | | |
| H$_2$O | | 35.30 | 19.00 | 37.83 | 0.32 | 0.07 | | 99.14 | 100.00 |

| Comp., Mole % | Pos. 9 | Pos. 10 | Pos. 11 | Pos. 12 | Pos. 13 | Pos. 14 | Pos. 15 | Pos. 16 |
|---|---|---|---|---|---|---|---|---|
| Ar | | | | | | | | |
| C$_2$H$_6$ | | | | | | | | |
| CH$_4$ | | | | 0.01 | | 0.01 | | |
| CO | | | | 0.01 | | 0.01 | | |
| CO$_2$ | | 0.21 | | 91.72 | | 91.72 | | |
| H$_2$ | | 0.05 | | 0.18 | | 0.18 | 0.08 | |
| N$_2$ | | | | | | | 0.06 | |
| CH$_3$OH | | 0.76 | | 0.06 | | 0.06 | | |
| NH$_3$ | | | | | 99.81 | | 99.86 | |
| H$_2$O | 100.00 | 98.98 | 100.00 | 8.02 | 0.19 | 8.02 | | |
| CH$_4$N$_2$O | | | | | | | | 100.00 |

EXAMPLE 2 REDUCED UREA PRODUCTION

The below positions refer to the inlet of the units.

TABLE 3

Flows and operating conditions for FIG. 1

| | Position | | | | | | | | |
|---|---|---|---|---|---|---|---|---|---|
| | Pos. 1 | Pos. 2 | Pos. 3 | Pos. 4 | Pos. 5 | Pos. 6 | Pos. 7 | Pos. 8 | Pos. 9 |
| Temp., ° C. | 380 | 465 | 340 | 325 | 68 | 20 | 46 | 45 | 381 |
| Pressure, kg/cm$^2$ g | 47.9 | 42.4 | 37.1 | 37.1 | 34.3 | 33.6 | 185 | 51.5 | 45.9 |
| Flow, Nm$^3$/h | 147,025 | 227,249 | 498,691 | 545,746 | 481,494 | 382,357 | 440,547 | 67,158 | 42,981 |

| | Position | | | | | | |
|---|---|---|---|---|---|---|---|
| | Pos. 10 | Pos. 11 | Pos. 12 | Pos. 13 | Pos. 14 | Pos. 15 | Pos. 16 |
| Temp., ° C. | 256 | 380 | 50 | −32 | 50 | 20 | |
| Pressure, kg/cm$^2$ g | 43.8 | 45.9 | 0.5 | 8.2 | 0.5 | 32.2 | |
| Flow, Nm$^3$/h | 47,055 | 82,715 | 0 | 31,119 | 102,655 | 188,554 | 94,145 |

TABLE 4

Stream compositions, Positions refer to FIG. 1

| Comp., Mole % | Pos. 1 | Pos. 2 | Pos. 3 | Pos. 4 | Pos. 5 | Pos. 6 | Pos. 7 | Pos. 8 | Pos. 9 |
|---|---|---|---|---|---|---|---|---|---|
| Ar | | | 0.07 | 0.07 | 0.07 | 0.09 | | | |
| C$_2$H$_6$ | 0.06 | 0.04 | | | | | | | |
| CH$_4$ | 90.83 | 58.76 | 1.27 | 1.16 | 1.31 | 1.64 | | | |
| CO | | | 21.46 | 19.61 | 6.46 | 8.10 | | | |
| CO$_2$ | | | 4.08 | 3.75 | 19.97 | 20 ppm | | 0.22 | |
| H$_2$ | 3.25 | 2.11 | 52.49 | 47.97 | 70.10 | 87.84 | 75.00 | 0.03 | |
| N$_2$ | 5.86 | 3.79 | 1.73 | 1.57 | 1.80 | 2.26 | 25.00 | | |
| CH$_3$OH | | | | 0.06 | 0.01 | | | 0.48 | |
| NH$_3$ | | | | | | | | | |
| H$_2$O | | 35.30 | 18.90 | 25.81 | 0.28 | 0.07 | | 99.27 | 100.00 |

TABLE 4-continued

| Stream compositions, Positions refer to FIG. 1 | | | | | | | | |
|---|---|---|---|---|---|---|---|---|
| Comp., Mole % | Pos. 9 | Pos. 10 | Pos. 11 | Pos. 12 | Pos. 13 | Pos. 14 | Pos. 15 | Pos. 16 |
| Ar | | | | | | | | |
| $C_2H_6$ | | | | | | | | |
| $CH_4$ | | | | 0.01 | | 0.01 | | |
| CO | | | | 0.01 | | 0.01 | | |
| $CO_2$ | | 0.15 | | 91.71 | | 91.71 | | |
| $H_2$ | | 0.05 | | 0.20 | | 0.20 | 0.08 | |
| $N_2$ | | | | | | | 0.06 | |
| $CH_3OH$ | | 0.68 | | 0.05 | | 0.05 | | |
| $NH_3$ | | | | | 99.81 | | 99.86 | |
| $H_2O$ | 100.00 | 99.12 | 100.00 | 8.02 | 0.19 | 8.02 | | |
| $CH_4N_2O$ | | | | | | | | 100.00 |

I.e. For Example 2 this Means:
 Prereformer: Tin/Tout: 465/427° C. (ΔT=−1° C.)
 Steam/carbon ratio, S/C=0.6 inlet the prereformer
ATR:
 The process gas enters the ATR at 650° C. and the temperature of the oxygen is around 230° C.
 Steam/carbon ratio, S/C=0.7 as per definition in the description
 The process gas leaves the reforming section at about 1050° C. through a refractory lined outlet section and transfer line to the waste heat boilers in the process gas cooling section.
Shift Section:
 Steam containing shift reaction byproducts is added to the synthesis gas inlet the high temperature shift changing the steam/carbon ratio to 1.0 and the methanol content from 0 to 320 Nm³/h, position 4
 The shift section consists of two high temperature shift step
  HT(1): Tin/Tout: 325/449° C. (ΔT=124° C.)
  HT(2): Tin/Tout: 340/368° C. (ΔT=28° C.)
 After reforming, about 26.5 vol % CO is present in the gas (dry basis). In the first high temperature shift converter the CO content is reduced to approximately 9.8 vol %, and the temperature increases from 325° C. to 449° C. The heat content of the effluent from the high temperature CO converter is recovered in a waste heat boiler and in a boiler feed water preheater.
 The process gas is thereby cooled to 340° C. and passed on to the second high temperature shift converter in which the CO content is reduced to approximately 6.5 vol %, while the temperature increases to 368° C.
 The methanol content exit the shift section is 368 Nm³/h.
Synthesis Gas Wash
 After the shift section the synthesis gas is cooled and washed with water The methanol content in the synthesis gas, position 5 leaving the synthesis gas wash is 47.7 Nm³/h after separation of the process condensate and washing water
Process Condensate Stripper
 The process condensate and washing water is stripped with steam reducing the methanol in the process condensate and wash water from 320.5 Nm³/h, position 8 to 0.7 Nm³/h in in the stripped process condensate leaving the process condensate stripper.
 The stripper steam, position 10 leaving the condensate stripper contains 320 Nm³/h of methanol, which, in this example, all is added to the shift section again as described above.

$CO_2$ Removal Section
 The $CO_2$ content in the outlet stream from shift section is reduced to 20 ppm. All Methanol in the synthesis gas going to the $CO_2$ removal section will leave this section with the $CO_2$ product stream, position 14 and/or 12.
$N_2$ Wash Section
 First step in this section is a quantitatively removal of $CO_2$ and $H_2O$ in a molecular sieve dryer. Next step is a $N_2$ liquid wash removing components other than $H_2$ and $N_2$ down to ppm level. The third step is to adjust the $H_2/N_2$ ratio to approximate 3 using gaseous nitrogen.
Syngas Compressor:
 The synthesis gas is compressed from 33.7 to 185.8 kg/cm²g in the centrifugal type two-casing synthesis gas compressor. Part of the last casing forms the recirculation compressor in the synthesis loop.
Inert Free Loop:
 The loop can be defined as inert when no purge gas system is required.
 The small amounts of inert gases entering the loop with the make-up synthesis gas will accumulate in the loop until the amount of inert gases dissolved in the liquid ammonia exit the let-down vessel equals the amount entering the loop. Off gas from the let-down vessel is recycled back to the synthesis gas compressor.
 The recycled inert level is dependent on the level of inerts dissolved in the liquid ammonia leaving the ammonia separator and the let-down vessel.
 If required the level of inert gas in the loop can be reduced by an intermittent purge of a small gas stream.
 In this example the inert level in the purified gas leaving the $N_2$ wash is 17 ppm Ar, in the make-up gas 53 ppm Ar (after addition of the off gas recycle stream from the let-down vessel) and 0.30% Ar inlet the converter.
 The example shows that the process described in the present invention reduces the methanol byproduct formation by 320/(320+48.4)*100=86.9%. Furthermore, the presented process ensures a content of methanol in the $CO_2$ stream, position 12 and/or 14, is less than what is obtained in typical known processes in operation today and enables reduction to lower levels should this be required.
 In example 1 109,675 Nm³/h $CO_2$ reacts with 219,350 Nm³/h $NH_3$ to produce 109,675 Nm³/h $CH_4N_2O_2$ corresponding to full urea production.

$$2NH_3 + CO_2 \leftrightarrow NH_2CONH_2 + H_2O + \text{heat} \quad (1)$$

In example 2 with reduced urea production 94,145 Nm³/h $CO_2$ is produced and reacts with 188,290 Nm³/h $NH_3$ to produce 94,145 Nm³/h $CH_4N_2O_2$. In this case 31,060 Nm³/h excess NH3 is sent to storage.

The two examples show the option of adjusting and thus tailor design the $CO_2$ production by steam addition and shift inlet temperature adjustment. If reduced urea production is requested less steam can be added and 2×HTS shift combination may be used. If full urea production is requested additional steam is added and HTS+MTS shift configuration may be used. Even an over stoichiometric amount of $CO_2$ can be produced if requested by adding more steam and adjusting the shift inlet temperatures to the shift stages appropriately.

In conventional ammonia/urea plants the $CO_2/NH_3$ ratio is defined by the feed gas composition. This means that excess $CO_2$ is typically vented if reduced urea production is requested. If full urea production is requested in conventional ammonia/urea plants part of the synthesis gas is used as fuel instead of ammonia production to adjust the $CO_2/NH_3$ ratio. This means a larger front end is required.

The invention claimed is:

1. A process for producing urea, said process comprising the steps of:
    optionally purifying a hydrocarbon feed gas to remove sulfur and/or chloride components if present,
    reforming the hydrocarbon feed gas in a reforming step with a steam/carbon molar ratio of 2-0.2, thereby obtaining a synthesis gas comprising $CH_4$, CO, $CO_2$, $H_2$ and $H_2O$,
    optionally adding $H_2O$ to the synthesis gas from the reforming step to maintain an overall steam/carbon molar ratio less than 2,
    shifting the synthesis gas in a shift section comprising one or more shift steps in series utilizing a zinc-aluminum oxide based catalyst, and operating the shift section at a steam/carbon molar ratio of less than 2.6,
    optionally cooling and/or adding $H_2O$ to the synthesis gas between the shift steps,
    optionally washing the synthesis gas leaving the shift section with water,
    removing $CO_2$ from the synthesis gas from the shift section in a $CO_2$ removal step to obtain a synthesis gas with less than 20 ppm $CO_2$ and a $CO_2$ product gas,
    removing residual $H_2O$ and/or $CO_2$ from the synthesis gas in an absorbent step,
    removing $CH_4$, CO, Ar and/or He from the synthesis gas in a nitrogen wash unit and adding stoichiometric nitrogen to the synthesis gas to produce $NH_3$ synthesis gas,
    synthesizing $NH_3$ from the $NH_3$ synthesis gas to obtain a $NH_3$ product,
    adding at least part of the product $CO_2$ and at least part of the $NH_3$ product to a urea synthesis step to make a urea product,
    wherein the amount of excess $CO_2$ and/or $NH_3$ is controlled by adjusting the steam/carbon molar ratio in the reforming step and/or adjusting $H_2O$ addition upstream and/or in between the shift steps and/or adjusting the inlet temperature to at least one of the one or more shift steps.

2. Process according to claim 1, wherein a process condensate, derived from the cooling of the synthesis gas between the shift steps and including methanol formed by the shift steps, is sent to a process condensate stripper, wherein dissolved shift byproducts and dissolved gases, including the methanol formed by the shift steps, are stripped out of the process condensate using steam, resulting in a steam stream, and wherein at least part of this steam stream is used as the $H_2O$ added upstream the shift section and/or between shift steps in the shift section.

3. Process according to claim 1, wherein the one or more shift steps are one or more high temperature (HT) shift steps, using a promoted zinc-aluminum oxide based catalyst.

4. Process according to claim 3, wherein the temperature in the high temperature shift step(s) is 300-600° C.

5. Process according to claim 3, wherein the promoted zinc-aluminum oxide based HT shift catalyst comprises Zn and Al in a Zn/Al molar ratio in the range 0.5 to 1.0 and a content of alkali metal in the range 0.4 to 8.0 wt % and a copper content in the range 0-10 wt%.

6. Process according to claim 1, wherein the steam/carbon molar ratio in the reforming step is 1.5-0.3.

7. Process according to claim 1, wherein the reforming takes place in an autothermal reformer (ATR).

8. Process according to claim 7, wherein the space velocity in the ATR is less than 20,000 $Nm^3$ $C/m^3/h$.

9. Process according to claim 1, further comprising a prereforming step.

10. Process according to claim 1, wherein the steam/carbon molar ratio in the reforming step is adjusted.

11. Process according to claim 1, wherein the shift section comprises one or more high temperature shift steps, one and more medium temperature shift steps and/or one or more low temperature shift steps, thereby obtaining a selected $CO_2$ content in the synthesis gas stream entering the $CO_2$ removal step.

12. Process according to claim 1, wherein steam is added to the synthesis gas before one or more of the shift steps in the shift section, thereby obtaining a selected $CO_2$ content in the synthesis gas stream entering the $CO_2$ removal step.

13. Process according to claim 1, wherein the inlet temperature to one or more of the one or more shift steps is adjusted, thereby obtaining a selected $CO_2$ content in the synthesis gas stream entering the $CO_2$ removal step.

14. Process according to claim 2, wherein the steam stream contains more than 90% of the methanol dissolved in the process condensate.

* * * * *